United States Patent
Grandjean

(10) Patent No.: US 6,839,592 B2
(45) Date of Patent: Jan. 4, 2005

(54) CARDIAC RESYNCHRONIZATION WITH ADAPTIVE A1-A2 AND/OR V1-V2 INTERVALS

(75) Inventor: Pierre Grandjean, Warsage (BE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/126,516

(22) Filed: Apr. 22, 2002

(65) Prior Publication Data

US 2003/0199930 A1 Oct. 23, 2003

(51) Int. Cl.[7] .................................................. A61N 1/36
(52) U.S. Cl. ......................................... 607/9; 607/14
(58) Field of Search ............................ 607/9, 17, 4, 14

(56) References Cited

U.S. PATENT DOCUMENTS 6,567,700 B1 * 5/2003 Turcott et al. .................. 607/9

2001/0031993 A1   10/2001   Salo et al.

FOREIGN PATENT DOCUMENTS

| EP | 1142607 | 10/2001 | .......... A61N/1/368 |
| EP | 1155711 | 11/2001 | ............ A61N/1/37 |
| EP | 1155712 | 11/2001 | ............ A61N/1/37 |
| WO | WO 01/36042 | 5/2001 | .......... A61N/1/362 |

* cited by examiner

Primary Examiner—Angela D. Sykes
Assistant Examiner—Roderick Bradford
(74) Attorney, Agent, or Firm—Girma Wolde-Michael; Paul H. McDowall

(57) ABSTRACT

In a system that provides bi-atrial and/or bi-ventricular pacing, the system adjusts an interval between paces delivered to the atria, and/or an interval between paces delivered to the ventricles, as a function of heart rate. By adjusting the interval between paces as a function of heart rate, the atria and/or ventricles may be activated in a more synchronous and more hemodynamically efficient fashion.

20 Claims, 9 Drawing Sheets

CARDIAC RESYNCHRONIZATION WITH ADAPTIVE A1-A2 AND/OR V1-V2 INTERVALS

FIELD OF THE INVENTION

The invention relates to cardiac pacing systems, and more particularly to multiple-chamber cardiac pacing systems.

BACKGROUND

Many patients that suffer from congestive heart failure (CHF) develop a wide QRS complex resulting from a delayed activation of one of the ventricles in the heart, and inter- and/or intraventricular electrical-mechanical dysynchrony. This ventricular "dysynchrony" may be caused by dilation of the heart, which disrupts the conductive pathways and interferes with depolarization sequences. Ventricular dysynchrony may worsen heart failure symptoms.

In a classic case of ventricular dysynchrony, the patient's right ventricle activates first, and the left ventricle activates at a later time. The patient often experiences a reduction in cardiac output because the ventricles begin contraction at slightly different times. The timing imbalance may also cause the patient to experience paradoxical septal motion, mitral regurgitation or decreased ventricular filling time.

Patients having a wide QRS complex or having inter- and/or intraventricular electrical-mechanical dysynchrony may receive benefits from an implanted medical device, such as a pacemaker, that paces both ventricles. The implanted medical device senses or paces atrial contractions, waits a predetermined time (or atrioventricular (AV) delay) after each sensed or paced atrial contraction, and then paces both ventricles. The ventricles may be paced simultaneously, or one ventricle may be paced before another. This bi-ventricular pacing is one form of cardiac resynchronization, and it provides many CHF patients with improvements in quality of life, exercise capacity and overall cardiac function.

Generally speaking, cardiac resynchronization refers to pacing therapies applied by implanted medical devices with one or more pacing leads in two or more complementary chambers of the heart. For purposes of the following discussion, the right and left atria are complementary to one another, and the right and left ventricles are complementary chambers. The right and left atria are complementary because they are the upper chambers that receive blood and transfer it to the ventricles. The right and left ventricles are complementary chambers because they receive blood from the atria and pump the blood to the heart. In a heart in a healthy patient, complementary chambers activate at approximately the same time. In a heart in a patient suffering from a condition such as CHF, complementary chambers activate at different times.

The right and left atria are complementary because they are the upper chambers that receive blood and transfer it to the ventricles. The right and left ventricles are complementary chambers because they receive blood from the atria and pump the blood to the heart. In a heart in a healthy patient, complementary chambers activate at approximately the same time. In a heart in a patient suffering from a condition such as CHF, complementary chambers activate at different times.

In response to a sensed or paced event, the pacemaker delivers pacing pulses or stimulations to two complementary chambers of the heart. The pacing pulses may be, but need not be, delivered simultaneously. Although the discussion that follows emphasizes bi-ventricular pacing to treat ventricular dysynchrony, cardiac resynchronization also encompasses, for example, resynchronization of atrial contractions.

Multiple-chamber pacing systems in general, and bi-ventricular and bi-atrial pacing systems in particular, are known in the art. Prior art techniques for synchronizing ventricles or atria are generally imprecise, however, and are not adaptive to changing conditions. In a typical bi-ventricular pacemaker that delivers pacing pulses to the ventricles at different times, for example, the time interval between delivery of the pacing pulses may be fixed and not automatically adjustable.

Examples of these techniques and/or devices may be found in the issued U.S. patents listed in Table 1 below.

TABLE 1

| U.S. Pat. No. | Inventor | Issue Date |
|---|---|---|
| 5,540,727 | Tockman et al. | Jul. 30, 1996 |
| 5,792,203 | Schroeppel | Aug. 11, 1998 |
| 6,021,351 | Kadhiresan et al. | Feb. 01, 2000 |
| 6,070,101 | Struble et al. | May 30, 2000 |
| 6,081,748 | Struble et al. | Jun. 27, 2000 |
| 6,122,545 | Struble et al. | Sep. 19, 2000 |
| WO 99/55415 | Struble et al. | Nov. 04, 1999 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to multiple-chamber cardiac pacemakers, such as pacemakers that provide bi-ventricular or bi-atrial pacing. These problems include, for example, an inability to adapt a pacing interval to current cardiac conditions to promote hemodynamic efficiency, and an inability to adapt a pacing interval to changing cardiac conditions. Various embodiments of the present invention have the object of solving at least one of the foregoing problems.

It is an object of the invention to select a time interval, separating pacing pulses to the ventricles or the atria, that promotes hemodynamic efficiency. The invention may be applied to bi-ventricular pacing, bi-atrial pacing, or any combination thereof. In the context of bi-ventricular pacing, for example, the interval between pacing pulses delivered to the ventricles may be called the "V1-V2 interval." In some patients, simultaneous stimulation of the ventricles results in a lack of ventricular synchrony.

The lack of synchrony may be caused by factors such as differences in placement of stimulating electrodes proximate to the ventricles or the differences in the conductive pathways of the ventricles. The lack of synchrony may cause the ventricles to begin ejection of blood at different times. For some patients, asynchronous blood ejection is inefficient and undesirable. The techniques of the invention bring the ventricles into synchrony, resulting in improved hemodynamic performance.

Realization of synchrony at one heart rate, however, does not assure synchrony at another heart rate. When a patient increases his activity, his pacemaker may pace the heart at a faster rate to meet the new biological demand upon the heart. An increase in activity may be accompanied by a sympathetic activation, which may affect the conductive properties of the heart. As a result of the change in heart rate, therefore, a pacing interval that produced synchrony at a lower heart rate may fail to produce synchrony at a higher heart rate. Accordingly, it is also an object of the invention to select a pacing interval, such as a V1-V2 interval, that realizes synchrony at different heart rates.

It is a further object of the invention that the techniques be adaptable to bi-atrial pacing. Accordingly, the techniques of the invention may also be applied to adjust the "A1-A2 interval," which represents the time delay between delivery of pacing pulses to the atria. Another object of the invention is that the techniques be adaptable to patients who need both bi-atrial pacing and bi-ventricular pacing. Accordingly, the techniques of the invention may be applied to both the A1-A2 interval and the V1-V2 interval employed by a four-chamber pacemaker.

An additional object of the invention is that adjustment of one or more pacing intervals may be performed automatically. In particular, pacing intervals such as the V1-V2 interval may be adjusted in response to changing heart rate. The invention presents techniques for resynchronizing cardiac chambers in response to changes in heart rate. The heart rate may change in response to changes in patient activity.

Various embodiments of the invention may possess one or more features capable of fulfilling the above objects. In general, the invention includes a pacemaker that provides multi-chamber pacing. In particular, the pacemaker provides bi-atrial pacing, bi-ventricular pacing, or both. The invention may include a processor that computes a V1-V2 interval and/or an A1-A2 interval such that pacing pulses, separated by this interval, cause the corresponding chambers to work in synchrony. In a typical bi-ventricular application, the processor may select the V1-V2 interval to cause the right and left ventricles to commence blood ejection at the same time. The processor may further adjust the interval in response to changes in heart rate, which in turn may be responsive to changes in patient activity sensed with an activity sensor.

The invention may offer one or more advantages. By selection of an interval that separates pacing pulses delivered to the ventricles or to the atria, the chambers of the heart may be synchronized for near-optimal cardiac performance. When the chambers are synchronized, the patient may experience improved cardiac performance, such as improved stroke volume and cardiac output. Moreover, the chambers of the heart may be resynchronized for near-optimal cardiac performance in response to changes in heart rate that may accompany changes in activity. In this manner, resynchronization can be achieved over a range of patient activity.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
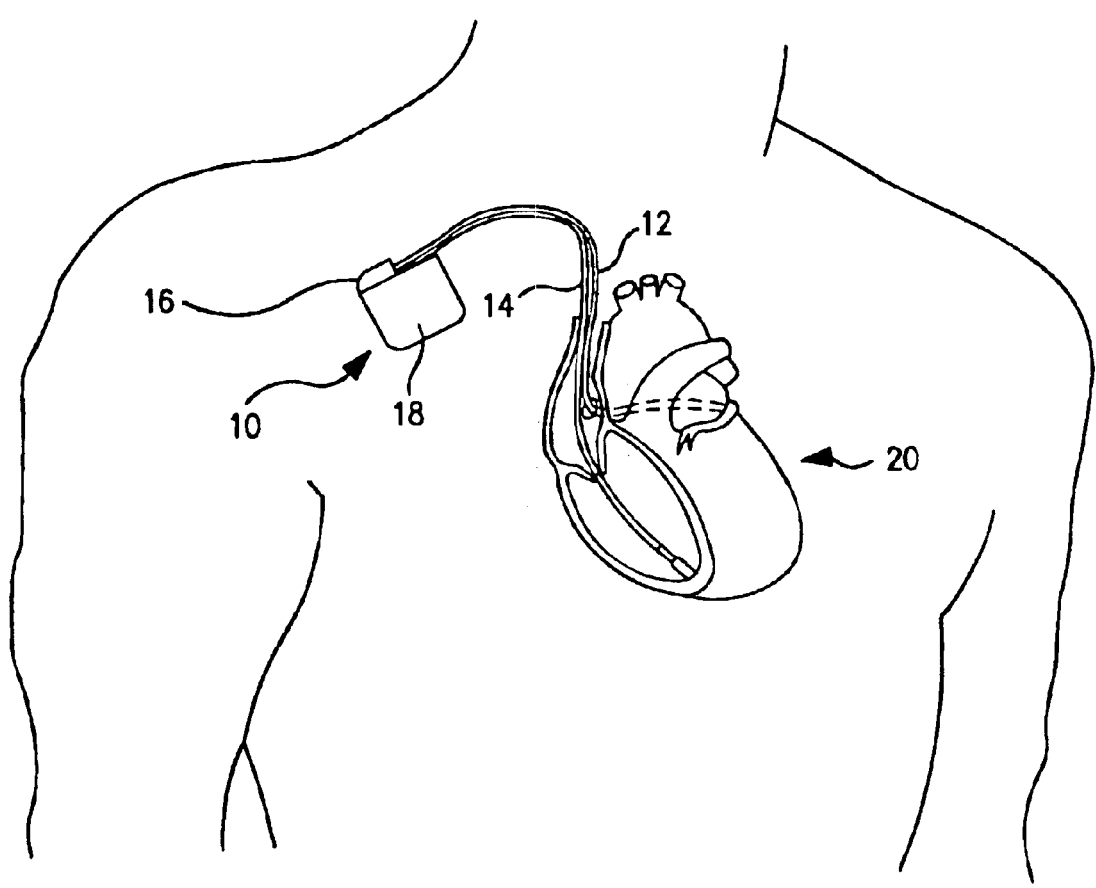
FIG. 1 is a schematic view of an exemplary implantable medical device.

FIG. 1 is a simplified schematic view of pacemaker 10, which is one embodiment of an implantable medical device of the present invention. Pacemaker 10 shown in FIG. 1 comprises at least one of pacing and sensing leads 12 and 14 attached to connector module 16 of hermetically sealed housing 18 and implanted near human or mammalian heart 20. Pacing and sensing leads 12 and 14 sense electrical signals attendant to the depolarization and repolarization of the heart 20, and further provide pacing pulses for causing depolarization of cardiac tissue in the vicinity of the distal ends thereof. Leads 12 and 14 may have unipolar or bipolar electrodes disposed thereon, as is well known in the art. Examples of pacemaker 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
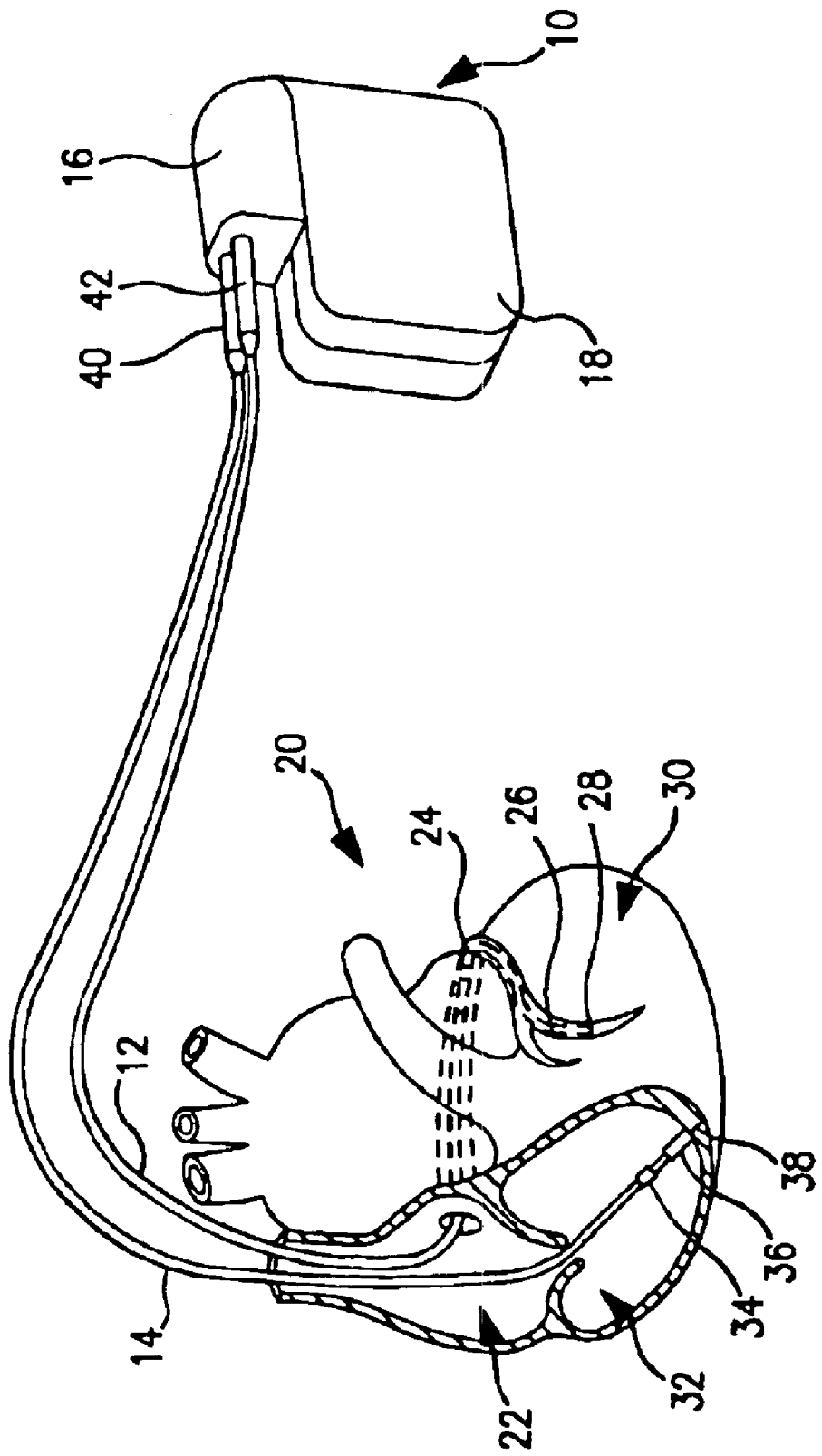
FIG. 2 shows the exemplary implantable medical device of FIG. 1 located in and near a heart.

FIG. 2 is a schematic representation of an exemplary implanted, two-channel cardiac pacemaker 10 in which the invention may be practiced. Pacemaker 10 is shown in conjunction with a human heart 20. Bipolar, endocardial left ventricular (LV) coronary sinus lead 12 is passed through a vein into the right atrium 22 of heart 20, into the coronary sinus 24 and then inferiorly in the great vein and cardiac veins extending from coronary sinus 24 to extend the distal ring pace/sense electrodes 26 and 28 alongside the LV chamber 30. The distal end of LV coronary sinus lead 12 positions ring electrodes 26 and 28 optimally with respect to the adjacent wall of left ventricle 30. Bipolar, endocardial right ventricular (RV) lead 14 is passed through the vein into right atrium 22 and into the right ventricle 32 where its distal ring and tip pace/sense electrodes 34 and 36 are fixed in place in the apex or in the interventricular septum by a distal attachment mechanism 38.

Pace/sense electrodes 26, 28, 34 and 38 sense electrical signals attendant to the depolarization and repolarization of heart 20. The electrical signals are conducted to pacemaker 10 via leads 12 and 14. Pace/sense electrodes 26, 28, 34 and 38 further deliver pacing pulses for causing depolarization of cardiac tissue in the vicinity of the distal ends thereof. The pacing pulses are generated by pacemaker 10 and are transmitted to pace/sense electrodes 26, 28, 34 and 38 via leads 12 and 14.

RV lead 14 is formed with an in-line connector 40 fitting into a bipolar bore of pacemaker connector block 16. RV lead 14 includes a pair of electrically insulated conductors that couple distal tip pace/sense electrode 36 and proximal pace/sense ring electrode 34 to pacemaker 10. LV coronary sinus lead 12 is formed with an in-line connector 42 fitting into a bipolar bore of pacemaker connector block 16. LV coronary sinus lead 12 couples distal ring pace/sense electrode 28 and proximal pace/sense ring electrode 26 to pacemaker 10.

Pacemaker 10 may deliver pacing pulses to ventricles 30, 32. Although the pacing pulses may be delivered to both ventricles 30, 32 simultaneously, in many cases there is a delay between delivery of a pacing pulse to one ventricle and a pacing pulse to the other ventricle. This delay is called the V1-V2 interval.

In general, the object of the V1-V2 interval is to promote ventricular synchrony. Due to physiological differences such as differences in conductive paths in ventricles 30, 32, one ventricle may activate before the other when the ventricles are paced at the same time. The V1-V2 interval compensates for the physiological differences. Although the ventricles 30, 32 are paced at different times, they activate together. The hemodynamic performance of heart 20 is enhanced when ventricles 30, 32 activate synchronously.

In general, the invention presents techniques for detecting whether the ventricles are activating synchronously and adjusting the V1-V2 interval to restore synchronous activation. As will be described in more detail below, the invention may also apply to synchronous activation of the atria of heart 20.

The pacing system shown in FIG. 2 is exemplary. The invention is not limited to the electrode placements shown in FIG. 2. LV pace/sense electrodes 26 and 28, for example, may be located at a site other than coronary sinus 24. RV pace/sense electrodes 34 and 36 likewise may be located at a site other than inside right ventricle 32. For example, RV pace/sense electrodes 34 and 36 may be epicardial, rather than endocardial as shown in FIG. 2. The pacing system may also include alternate or additional leads that deploy electrodes elsewhere around ventricles 30, 32, or proximate to the atria for sensing or pacing.

Furthermore, the invention is not limited to the bipolar ventricular lead systems depicted in FIG. 2. The invention may be employed with unipolar lead systems that employ a single pace/sense electrode in the depicted positions proximate to right ventricle 32 and left ventricle 30. Unipolar electrodes may cooperate with a remote electrode formed as part of the outer surface of the hermetically sealed housing 18 of pacemaker 10.

Figure 3:
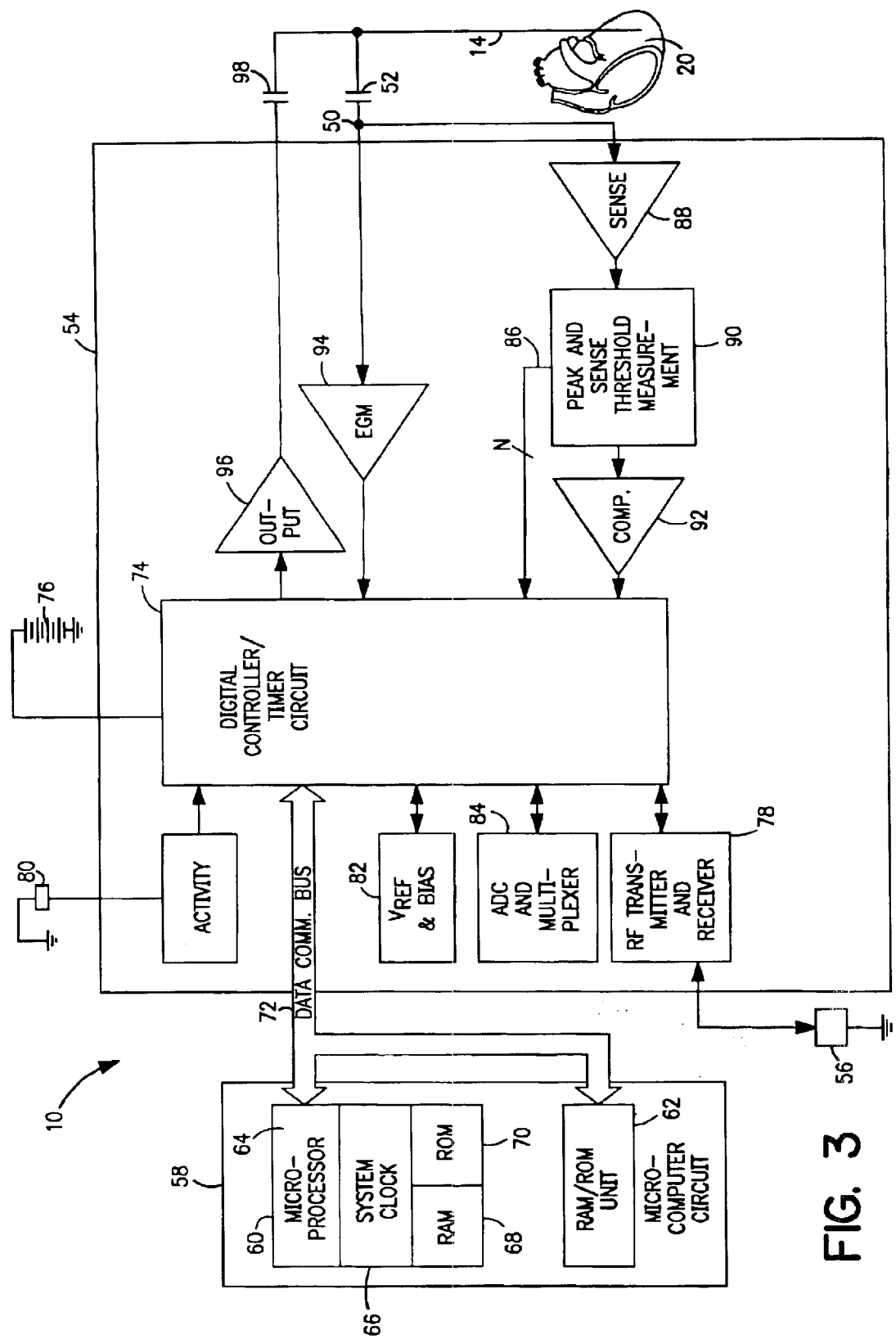
FIG. 3 is a block diagram illustrating the constituent components of the implantable medical device of FIGS. 1 and 2.

FIG. 3 shows a block diagram illustrating the constituent components of pacemaker 10 in accordance with one embodiment of the present invention. Pacemaker 10 is a pacemaker having a microprocessor-based architecture. Pacemaker 10 is shown as including activity sensor or accelerometer 44, which is preferably a piezoceramic accelerometer bonded to a hybrid circuit located inside housing 18 (shown in FIGS. 1 and 2). Activity sensor 44 typically (although not necessarily) provides a sensor output that varies as a function of a measured parameter relating to a patient's metabolic requirements. For the sake of convenience, pacemaker 10 in FIG. 3 is shown with lead 12 only connected thereto. However, it is understood that similar circuitry and connections not explicitly shown in FIG. 3 apply to lead 14 (shown in FIGS. 1 and 2).

Pacemaker 10 in FIG. 3 is most preferably programmable by means of an external programming unit (not shown in the figures). One such programmer is the commercially available Medtronic Model 9790 programmer, which is microprocessor-based and provides a series of encoded signals to pacemaker 10, typically through a programming head which transmits or telemeters radio-frequency (RF) encoded signals to pacemaker 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 12 is coupled to node 50 in pacemaker 10 through input capacitor 52. Activity sensor or accelerometer 44 is most preferably attached to a hybrid circuit located inside hermetically sealed housing 18 of pacemaker 10. The output signal provided by activity sensor 44 is coupled to input/output circuit 54. Input/output circuit 54 contains analog circuits for interfacing with heart 20, activity sensor 44, antenna 56 and circuits for the application of stimulating pulses to heart 20. The rate of heart 20 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board random access memory (RAM) 68 and read-only memory (ROM) 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of pacemaker 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of pacemaker 10 are coupled from microprocessor 64 via data bus 72 to digital controller/timer circuit 74, where digital timers and counters establish the overall escape interval of the pacemaker 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 14. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 86 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when pacemaker 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 12 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 12.

In some preferred embodiments of the present invention, pacemaker 10 may operate in various non-rate-responsive modes. In other preferred embodiments of the present invention, pacemaker 10 may operate in various rate-responsive modes. Some embodiments of the present invention are capable of operating in both non-rate-responsive and rate-responsive modes. Moreover, in various embodiments of the present invention pacemaker 10 may be programmably configured to operate so that it varies the rate at which it delivers stimulating pulses to heart 12 in response to one or more selected sensor outputs being generated. Numerous pacemaker features and functions not explicitly mentioned herein may be incorporated into pacemaker 10 while remaining within the scope of the present invention.

The present invention is not limited in scope to any particular number of sensors, and is not limited to pacemakers comprising activity or pressure sensors only. Although the present invention is useful in multiple-chamber pacemakers, the present invention is not limited in scope to pacemakers having any particular number of sensors per lead. At least some embodiments of the present invention may be applied equally well in the contexts of dual-, triple- or quadruple-chamber pacemakers or other types of pacemakers. See, for example, U.S. Pat. No. 5,800,465 to Thompson et al., hereby incorporated by reference herein in its entirety, as are all U.S. patents referenced therein.

Pacemaker 10 may also be a pacemaker combined with a cardioverter and/or defibrillator. Various embodiments of the present invention may be practiced in conjunction with a pacemaker-cardioverter-defibrillator such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
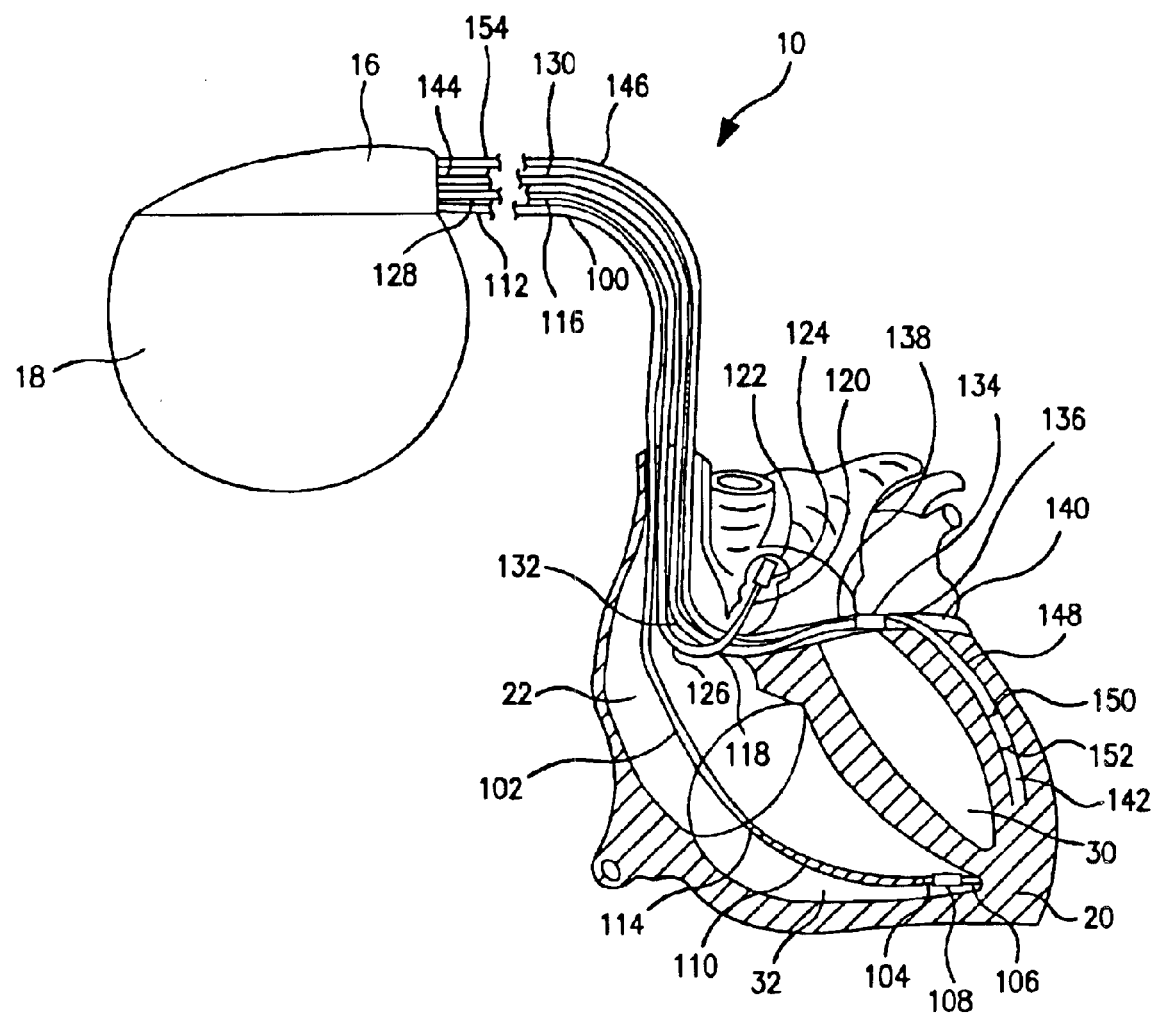
FIG. 4 shows an exemplary implantable multi-chamber medical device located in and near a heart.
Figure 5:
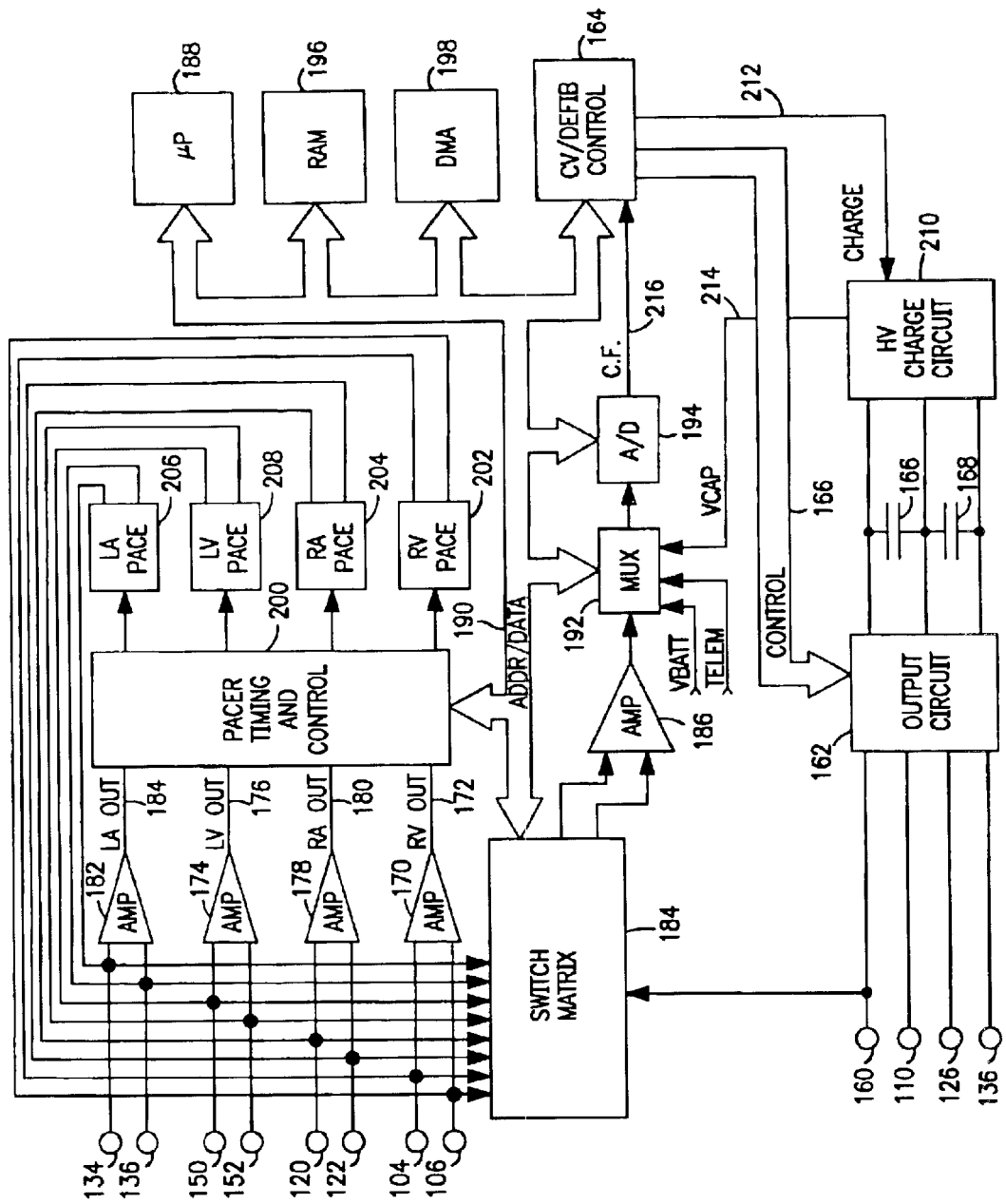
FIG. 5 is a functional schematic diagram of the embodiment of an implantable medical device shown in FIG. 4.

FIGS. 4 and 5 illustrate one embodiment of IMD 10 and a corresponding lead set of the present invention, where IMD 10 is a multi-chamber pacemaker-cardioverter-defibrillator. In FIG. 4, the right ventricular lead 100 may take the form of leads disclosed in U.S. Pat. Nos. 5,099,838 and 5,314,430 to Bardy, and includes an elongated insulative lead body 102 carrying three or more concentric coiled conductors separated from one another by tubular insulative sheaths. Located adjacent the distal end of lead 102 are ring electrode 104, extendable helix electrode 106 mounted retractably within insulative electrode head 108 and elongated coil electrode 110. Each of the electrodes is coupled to one of the coiled conductors within lead body 102. Electrodes 104 and 106 are employed for cardiac pacing and for sensing ventricular depolarizations. At the proximal end of lead 102 is a connector 112 which carries electrical connectors coupled to one of the coiled conductors. Elongated coil electrode 110, which is a defibrillation electrode 110, may be fabricated from platinum, platinum alloy or other materials known to be usable in implantable defibrillation electrodes and may be about 5 cm in length.

The atrial/SVC lead 116 shown in FIG. 4 includes elongated insulative lead body 118 carrying three concentric coiled conductors separated from one another by tubular insulative sheaths corresponding to the structure of ventricular lead 100. Located adjacent the J-shaped distal end of the lead are ring electrode 120 and extendable helix electrode 122 mounted retractably within an insulative electrode head 124. Each of the electrodes is coupled to one of the coiled conductors within lead body 118. Electrodes 122 and 120 are employed for atrial pacing and for sensing atrial depolarizations. Elongated coil electrode 126 is provided proximate to electrode 120 and coupled to the third conductor within lead body 118. Electrode 126 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is connector 128 carrying three electrical connectors, each coupled to one of the coiled conductors.

The coronary sinus lead 130 shown in FIG. 4 assumes the form of a coronary sinus lead disclosed in the above cited '838 patent issued to Bardy, and includes elongated insulative lead body 132 carrying one or more coiled conductors coupled to a ring electrodes 134 and 136 and an elongated coiled defibrillation electrode 138. Electrodes 134, 136 are employed for atrial pacing and for sensing atrial depolarizations. Electrodes 134, 136, 138 are located within the coronary sinus 140 and great vein 142 of heart 20. At the proximal end of the lead 130 is connector plug 144 carrying an electrical connector coupled to the coiled conductor. Elongated coil defibrillation electrode 132 may be about 5 cm in length.

The left ventricular lead 146 may include elongated insulative lead body 148 carrying one or more coiled conductors coupled to a ring electrodes 150 and 152. Electrodes 150, 152 are employed for ventricular pacing and for sensing ventricular depolarizations. Electrodes 150, 152 are located within the great vein 140 of heart 20. At the proximal end of the lead 146 is connector plug 154 carrying an electrical connector coupled to the coiled conductor.

IMD 10 is shown in FIG. 4 in combination with leads 100, 116, 130, 146, and lead connector assemblies 112, 128, 144, 154 inserted into connector module 16. Optionally, insulation of the outward facing portion of housing 18 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 18 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 160 in FIG. 5 includes the uninsulated portion of the housing 18 of IMD 10. Electrodes 110, 126, 136 and 160 are coupled to high voltage output circuit 162, which includes high voltage switches controlled by CV/defib control logic 164 via control bus 166. Switches disposed within circuit 162 determine which electrodes are employed and which electrodes are coupled to the positive and negative terminals of a capacitor bank (which includes capacitors 166 and 168) during delivery of defibrillation pulses.

Electrodes 104 and 106 are located on or in the right ventricle of the patient and are coupled to the R-wave amplifier 170, which preferably takes the form of an automatic gain controlled amplifier providing an adjustable sensing threshold as a function of the measured R-wave amplitude. A signal is generated on R-out line 172 whenever the signal sensed between electrodes 104 and 106 exceeds the present sensing threshold.

Similarly, electrodes 150 and 152 are located proximate to the left ventricle of the patient and are coupled to the R-wave amplifier 174, which preferably also takes the form of an automatic gain controlled amplifier providing an adjustable sensing threshold as a function of the measured R-wave amplitude. A signal is generated on R-out line 176 whenever the signal sensed between electrodes 150 and 152 exceeds the present sensing threshold.

Electrodes 120 and 122 are located on or in the right atrium of the patient and are coupled to the P-wave amplifier 178, which preferably also takes the form of an automatic gain controlled amplifier providing an adjustable sensing threshold as a function of the measured P-wave amplitude. A signal is generated on P-out line 180 whenever the signal sensed between electrodes 120 and 122 exceeds the present sensing threshold.

Similarly, electrodes 134 and 136 are located proximate to the left atrium of the patient and are coupled to the P-wave amplifier 182, which preferably also takes the form of an automatic gain controlled amplifier providing an adjustable sensing threshold as a function of the measured P-wave amplitude. A signal is generated on P-out line 184 whenever the signal sensed between electrodes 134 and 136 exceeds the present sensing threshold. The general operation of R-wave and P-wave amplifiers 170, 174, 178, 182 may correspond to that disclosed in U.S. Pat. No. 5,117,824 to Keimel et al., hereby incorporated by reference herein in its entirety.

Switch matrix 184 is used to select which of the available electrodes are coupled to wide band (0.5–200 Hz) amplifier 186 for use in digital signal analysis. Selection of electrodes is controlled by microprocessor 188 via data/address bus 190, which selections may be varied as desired. Signals from the electrodes selected for coupling to bandpass amplifier 186 are provided to multiplexer 192, and thereafter converted to multi-bit digital signals by A/D converter 194, for storage in random access memory 196 under control of direct memory access circuit 198. Microprocessor 188 may employ digital signal analysis techniques to characterize the digitized signals stored in random access memory 196 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 200 preferably includes programmable digital counters which control the basic time intervals associated with DDD, VVI, DVI, VDD, AAI, DDI and other modes of single and multi-chamber pacing well known to the art. Circuitry 200 also preferably controls escape intervals associated with anti-tachyarrhythmia pacing in both the atrium and the ventricle, employing any anti-tachyarrhythmia pacing therapies known to the art.

Intervals defined by pacing circuitry 200 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 188, in response to stored data in memory 196 and are communicated to pacing circuitry 200 via address/data bus 190. Pacer circuitry 200 also determines the amplitude of the cardiac pacing pulses under control of microprocessor 188.

During pacing, escape interval counters within pacer timing/control circuitry 200 are reset upon sensing of R-waves and P-waves as indicated by a signals on lines 172, 176, 180 and 184 and in accordance with the selected mode of pacing on time-out trigger generation of pacing pulses by pacer output circuitry 202, 204, 206 and 208, which are coupled to electrodes 104, 106, 120, 122, 134, 136, 150 and 152. Escape interval counters are also reset on generation of pacing pulses and thereby control the basic timing of cardiac pacing functions, including anti-tachyarrhythmia pacing. The durations of the intervals defined by escape interval timers are determined by microprocessor 188 via data/ address bus 190. The value of the count present in the escape interval counters when reset by sensed R-waves and P-waves may be used to measure the durations of R-R intervals, P-P intervals, P-R intervals and R-P intervals, which measurements are stored in memory 196 and used to detect the presence of tachyarrhythmias.

IMD 10 may provide bi-ventricular pacing or bi-atrial pacing or both. Further, IMD 10 may provide bi-ventricular pacing or bi-atrial pacing in combination with other pacing. For example, IMD 10 may pace one atrium and both ventricles, or one ventricle and both atria.

In bi-atrial pacing, IMD 10 may deliver pacing pulses to the atria, the pulses separated by a delay called the A1-A2 interval. In bi-ventricular pacing, IMD 10 may deliver pacing pulses to the ventricles separated by a V1-V2 interval. Pacer timing/control circuitry 200 may control the durations of the A1-A2 interval and the V1-V2 interval.

Microprocessor 188 most preferably operates as an interrupt driven device, and is responsive to interrupts from pacer timing/control circuitry 200 corresponding to the occurrence of sensed P-waves and R-waves and corresponding to the generation of cardiac pacing pulses. Those interrupts are provided via data/address bus 190. Any necessary mathematical calculations to be performed by microprocessor 188 and any updating of the values or intervals controlled by pacer timing/control circuitry 200 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/8198, by Adams et al., and in the article "Automatic Tachycardia Recognition," by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 188 into the pacer timing and control circuitry 200, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 188 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 188 activates cardioversion/defibrillation control circuitry 164, which initiates charging of high voltage capacitors 166 and 168 via charging circuit 210, under the control of high voltage charging control line 212. The voltage on the high voltage capacitors is monitored via VCAP line 214, which is passed through multiplexer 192 and in response to reaching a predetermined value set by microprocessor 188, results in generation of a logic signal on Cap Full (CF) line 216 to terminate charging. Thereafter, timing of the delivery of the defibrillation or cardioversion pulse is controlled by pacer timing/control circuitry 200. Following delivery of the fibrillation or tachycardia therapy microprocessor 188 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 162 under the control of control circuitry 164 via control bus 166. Output circuit 162 determines whether a monophasic or biphasic pulse is delivered, the polarity of the electrodes and which electrodes are involved in delivery of the pulse. Output circuit 162 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Although FIGS. 4 and 5 depict one electrode per cardiac chamber, the invention is not limited to a single pacing electrode per chamber. Rather, the invention may be applied to multi-chamber pacing in which there maybe two or more electrodes per chamber. For example, the invention may be applied to a bi-ventricular pacing system that includes a single electrode in the right ventricle, but three electrodes placed around the left ventricle, such as the left ventricular anterior-septum wall, the left ventricular lateral free wall, and the left ventricular posterior free wall. Multiple-site electrode placement with respect to a single cardiac chamber may, for some patients, result in more homogenous activation and homogenous mechanical response.

Figure 6:
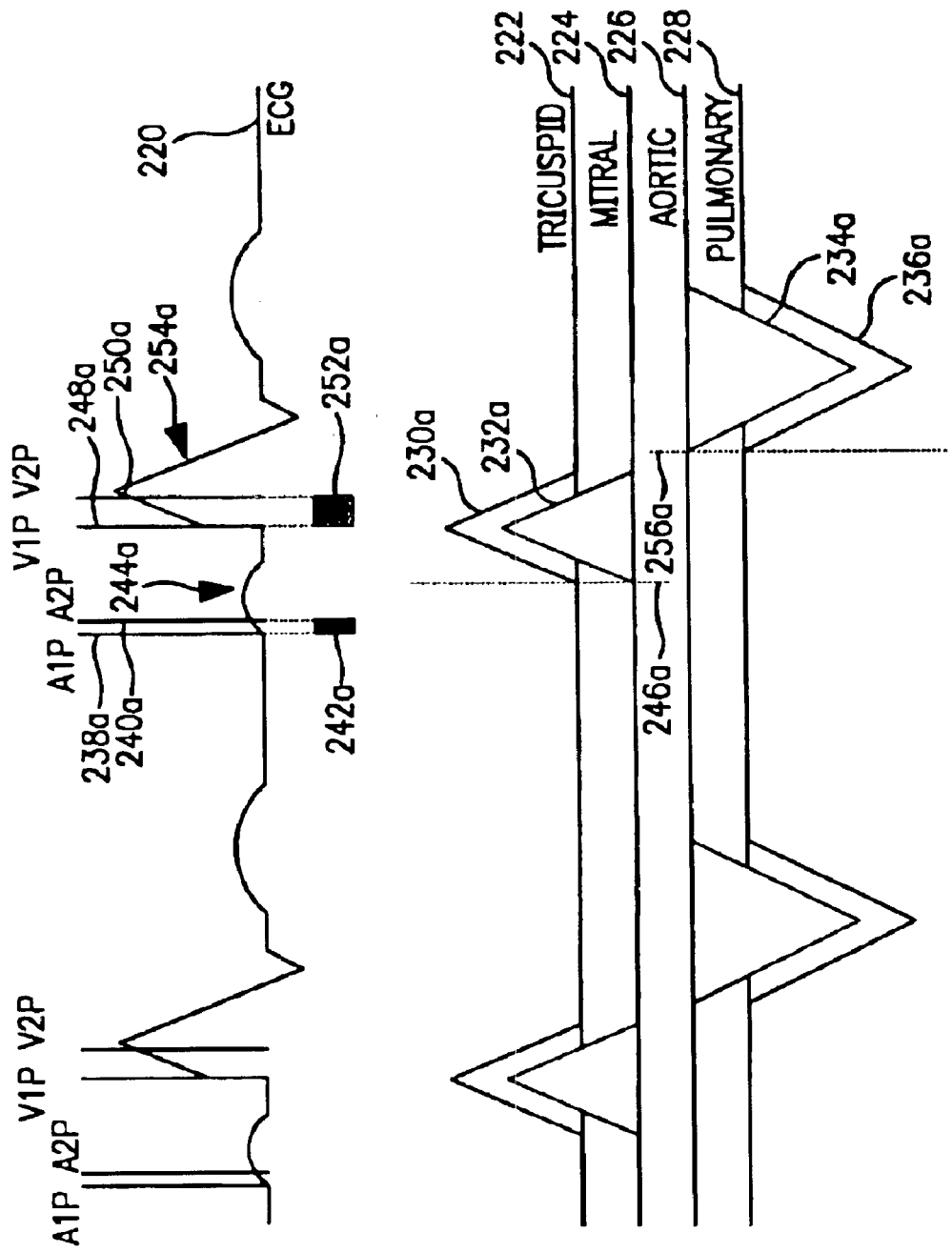
FIG. 6 is a timing diagram illustrating pacing of atria with an A1-A2 interval and pacing of ventricles with a V1-V2 interval, including four flow diagrams showing blood flow through the valves of the heart.
Figure 7:
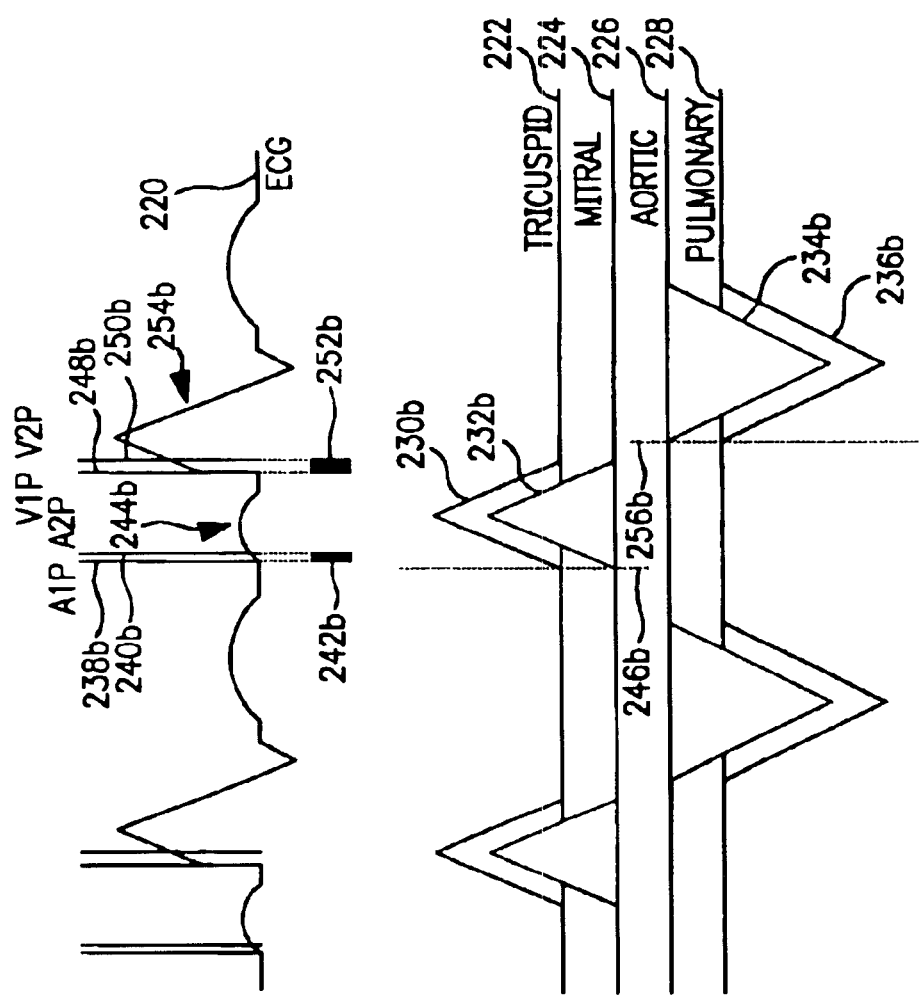
FIG. 7 is a timing diagram similar to FIG. 6, at a higher heart rate.

FIGS. 6 and 7 show timing diagram that illustrates an application of the invention. In FIGS. 6 and 7, the heart rate of the patient depends upon the frequency of pacing stimuli delivered to heart 20. In FIG. 6, the patient is being paced at a moderate rate, such as 60 paces per minute (ppm). Such a pacing rate may be appropriate for the ordinary activity of the patient. In FIG. 7, the patient is being paced at a more rapid rate, such as 100 ppm. A more rapid pacing rate may be appropriate when, for example, activity sensor or accelerometer 44 detects that the patient's metabolic requirements may be changing. In this manner, the invention may be applied to realize resynchronization over a range of patient activity. The patient's metabolic requirements may change, for example, during exercise or other exertion.

Units of "paces per minute" are in reference to number of paced cardiac cycles per minute, rather than a total number of pacing stimuli delivered to heart 20 in a minute. As will be described below, the illustrative timing diagrams in FIGS. 6 and 7 show four pacing stimuli per cardiac cycle.

In FIG. 6, an electrocardiogram (ECG) 200 is provided for reference. In addition, four flow diagrams 222, 224, 226, 228 show the blood flow through the valves of heart 20. Flow line 222 corresponds to the blood flow through the tricuspid, or right atrioventricular, valve, and flow line 224 corresponds to the blood flow through the mitral, or left atrioventricular, valve. Blood flow through the tricuspid valve caused by atrial contraction is represented by triangular wave 230*a*, and blood flow through the mitral valve caused by atrial contraction is represented by triangular wave 232*a*. Blood flow through the atrioventricular valves also includes blood flow caused by passive filling, but blood flow due to passive filling is not shown on FIG. 6.

Flow line 226 corresponds to the blood flow through the aortic valve, and triangular wave 234*a* represents the flow of blood through the aortic valve. Similarly, flow line 228 corresponds to the blood flow through the pulmonary valve, and triangular wave 236*a* represents the flow of blood through the pulmonary valve. The aortic and pulmonary valves are normally open only when the ventricles contract.

The atrial and ventricular contractions are responsive to atrial and ventricular paces.

In particular, the atria receive pacing pulses A1P 238*a* and A2P 240*a*, separated by an A1-A2 time interval 242*a*. The duration of interval 242*a* may be regulated by pacer timing/control circuitry 200 under control of microprocessor 188. A1-A2 time interval 242*a* may have a duration of, for example, twenty milliseconds. In response to atrial paces 238*a* and 240*a*, the atria depolarize, as reflected in P-wave 244*a*.

Atrial paces 238*a* and 240*a* cause the atria to eject blood into the ventricles, resulting in flow waves 230*a* and 232*a*. Although the atria receive pacing pulses at different times, the atria contract synchronously, causing blood flow to commence at the same time 246*a*. Synchronous ejection is, for many patients, a desirable result. When the atria eject blood simultaneously, the hemodynamic performance of the heart is, in many cases, nearly optimized.

The ventricles receive pacing pulses V1P 248*a* and V2P 250*a*, separated by a V1-V2 time interval 252*a*. The duration of interval 252*a* may be regulated by pacer timing/control circuitry 200 under control of microprocessor 188. In addition, the atrioventricular interval, i.e., the delay between delivery of atrial and ventricular pacing pulses, may be regulated by pacer timing/control circuitry 200 under control of microprocessor 188. In the example shown in FIG. 6, V1-V2 time interval 252*a* may have a duration of, for example, forty milliseconds. In response to ventricular paces 248*a* and 250*a*, the ventricles depolarize, as reflected in R-wave 254*a*.

Ventricular paces 248*a* and 250*a* cause the right ventricle to contract and eject blood into the pulmonary arteries, and the left ventricle to contract and eject blood into the aorta. Ventricular contraction causes aortic valve flow wave 234*a* and pulmonary flow wave 236*a*. The ventricles receive pacing pulses at different times, but the ventricles contract synchronously, causing blood ejection to commence at the same time 256*a*. As with atrial ejection, synchronous ventricular ejection is desirable for many patients, and results in near optimal hemodynamic performance.

In summary, the A1-A2 time interval 242*a* and V1-V2 time interval 252*a* achieve desirable results, with the ejection from the atria being synchronized and the ejection from the ventricles being synchronized. The fact that the A1-A2 time interval 242*a* and V1-V2 time interval 252*a* work well at a heart rate of 60 ppm, however, does not guarantee that the same A1-A2 time interval 242*a* and V1-V2 time interval 252*a* will work well at other heart rates.

When a patient increases his activity, the biological demand upon heart 20 changes. An increase in activity may be accompanied by a sympathetic activation, which may affect the conductive properties of heart 20. In general, sympathetic stimulation decreases conduction time throughout the heart. As a result, a pacing interval at one heart rate may result in simultaneous ejection from complementary chambers at one heart rate, but may cause dysynchrony at a higher heart rate, due to changes in the conductive pathways of heart 20.

When complementary chambers, particularly the ventricles, contract in an unsynchronized fashion, the patient may suffer a reduction of stroke volume in the short term and serious physiological changes to heart 20 in the longer term. The reduction in stroke volume is of concern because it affects cardiac output. When the patient experiences sympathetic stimulation, cardiac output should generally increase, due to increased heart rate and stroke volume. When the ventricles beat out of synchronization, however, stroke volume may be impaired and cardiac output may be too low for the level of activity, even if the heart rate is increased.

The invention is directed to techniques for adjusting one or more pacing intervals as a function of the heart rate, to maintain synchrony when the conductive properties of heart 20 change. An example of the technique is shown in FIG. 7, in which the patient has an elevated heart rate.

Like FIG. 6, FIG. 7 shows ECG 220 for reference, along with flow diagrams 222, 224, 226 and 228. The atria receive pacing pulses A1P 238b and A2P 240b, separated by an A1-A2 time interval 242b. A1-A2 time interval 242b may be of a shorter duration than A1-A2 time interval 242a in FIG. 6. In FIG. 7, A1-A2 time interval 242b may have a duration of, for example, ten milliseconds. Although A1-A2 time interval 242b may have a shorter duration than A1-A2 time interval 242a, atrial blood ejection is synchronous.

Similarly, ventricular pacing pulses V1P 248b and V2P 250b are separated by a V1-V2 time interval 252b, which may be of a shorter duration than V1-V2 time interval 252a. In FIG. 7, V1-V2 time interval 252b may have a duration of, for example, twenty milliseconds. Although V1-V2 interval 252b may have a shorter duration than V1-V2 time interval 252a, ventricular blood ejection is synchronous.

By adjusting the A1-A2 time interval and/or the V1-V2 time interval as a function of heart rate, synchronous ejection from complementary chambers may be maintained. In this way, the hemodynamic performance of the heart is maintained as conditions change. The patient does not experience a reduction of stroke volume due to ventricular dysynchrony.

Figure 8:
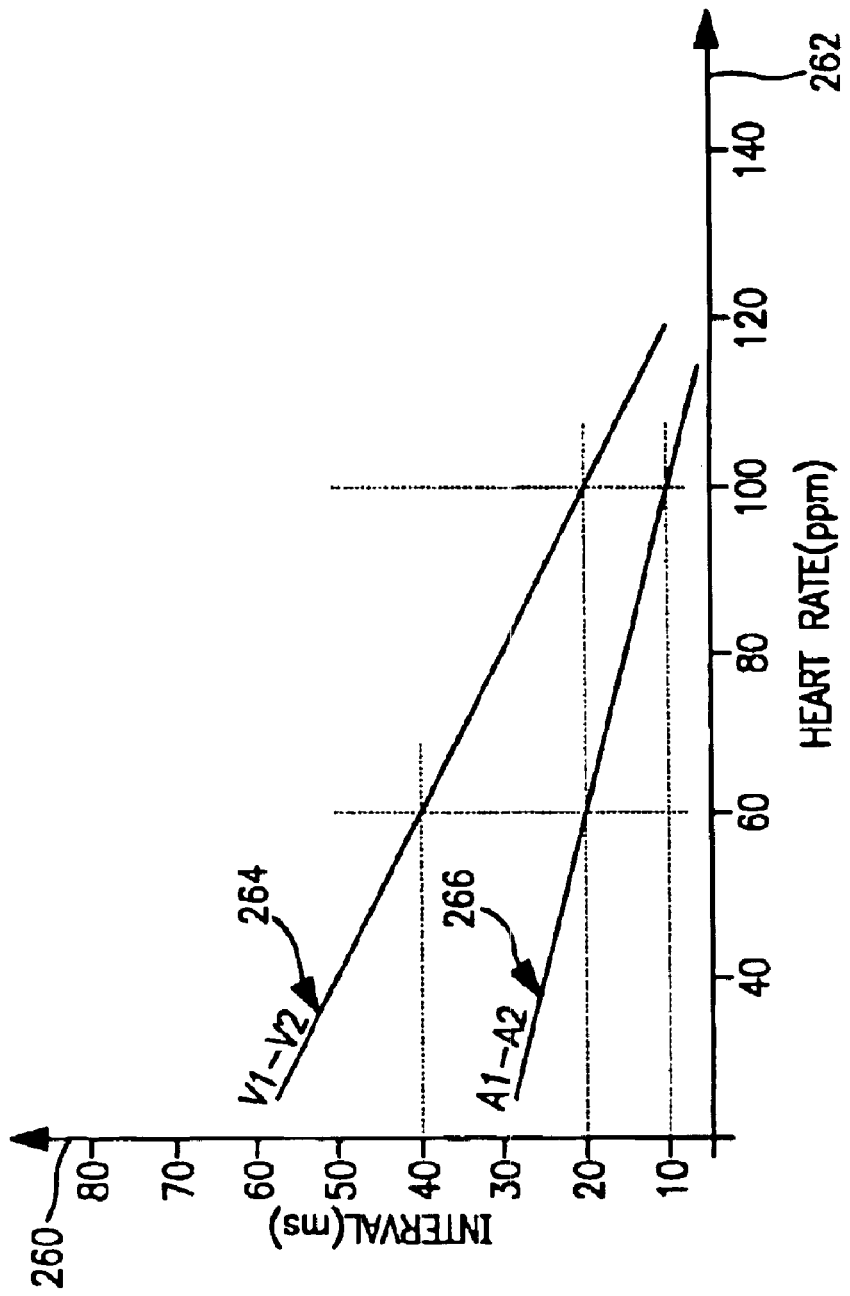
FIG. 8 is a graph illustrating exemplary pacing intervals as functions of heart rate.

FIG. 8 is an exemplary graph that illustrates selection of A1-A2 intervals and V1-V2 intervals 260 as a function of heart rate 262. Curve 264 shows an exemplary relationship between the V1-V2 interval and heart rate, and curve 266 shows an exemplary relationship between the A1-A2 interval and heart rate. Curves 264 and 266 illustrate the exemplary scenarios described above in connection with FIGS. 6 and 7. In particular, the V1-V2 interval is 40 ms and the A1-A2 interval is 20 ms at 60 ppm, and the V1-V2 interval is 20 ms and the A1-A2 interval is 10 ms at 100 ppm.

Curves 264, 266 may be substantially straight lines, as depicted in FIG. 8, but the invention is not limited to straight line relationships between intervals and heart rate. Curves 264, 266 may have any contour. Curves 264, 266 need not be continuous, but may, for example, relate a single interval to a range of heart rates.

The relationship between intervals and heart rate may be determined by the patient's physician. Any of a number of techniques may be used to collect the data that relate the intervals to the heart rate. For example, the physician may use echo-Doppler sensing techniques to determine the times that the valves of heart 20 are open. In general, echo-Doppler sensing may involve the use of ultrasound to observe the interior of heart 20 and locate a particular valve of interest. Once the valve is located, blood flow through the valve can be observed. In particular, pulsed-wave echo-Doppler techniques can be employed to observe the onset of blood flow, the speed and direction of the flow, the diameter of the valve, and the time flow stops.

The flow pattern may be measured with respect to another signal, such as an ECG signal that records the pacing pulses. In addition, the measurements may be repeated at several heart rates to determine how ejection times change as heart rate changes.

Another technique for finding a relationship between intervals and heart rate is to observe the cardiac output at several heart rates, and select intervals that produce a high cardiac output at each heart rate. Several techniques are available for estimating cardiac output, including measurement of blood oxygenation and measuring blood pressures in one or more chambers of heart 20. For some patients, simultaneous ejection may not necessarily lead to maximized cardiac output. By focusing upon cardiac output rather than ejection times, however, this technique may achieve superior hemodynamic performance even though ejection times may be slightly different. The invention encompasses setting intervals to increase cardiac output as well as to synchronize cardiac events.

Figure 9:
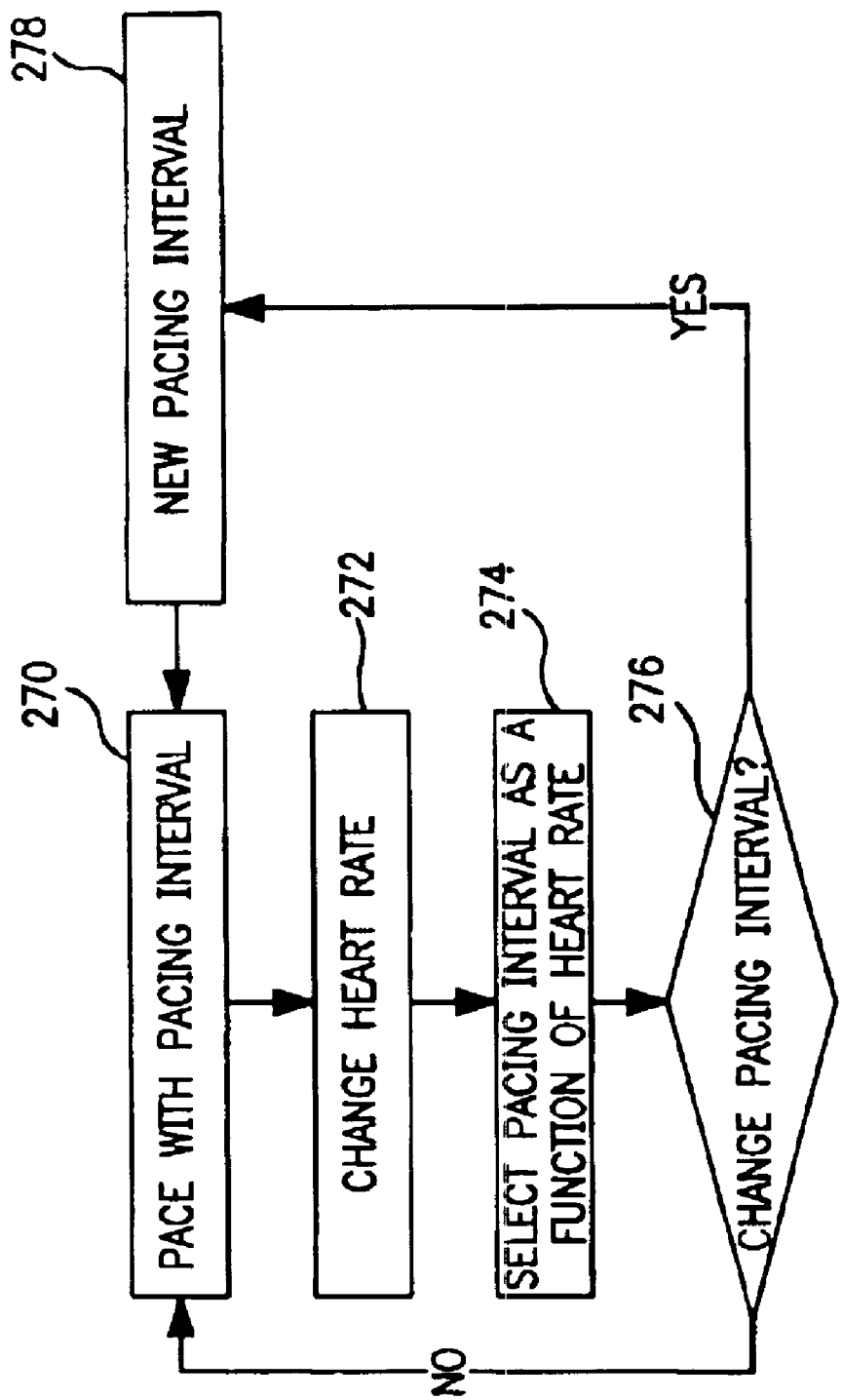
FIG. 9 is a flow diagram illustrating exemplary techniques for setting a V1-V2 interval and/or an A1-A2 interval in response to heart rate.

FIG. 9 illustrates techniques for adjusting the A1-A2 interval and/or the V1-V2 interval as a function of heart rate. Pacer timing/control circuitry 200 may be pacing at a first heart rate with a first A1-A2 and/or V1/V2 interval (270). When the rate of pacing increases (272), such as in response to data received from activity sensor 44, IMD 10 selects a pacing interval as a function of the new heart rate (274).

Microprocessor 188, for example, may perform the selection (274). In one implementation of the invention, a plurality of intervals may be stored in a lookup table in memory 196. Each interval may be mapped to a corresponding heart rate or range of heart rates. Microprocessor 188 may select an interval from the lookup table that corresponds to the new heart rate. In another implementation of the invention, an interval may be selected by application of a formula that defines the interval as a function of heart rate. Other techniques for selection of an interval as a function of heart rate are possible, and the invention encompasses all of them.

Optionally, IMD 10 may determine whether the new heart rate warrants a change in the pacing interval (276). In some circumstances, the pacing interval for the new heart rate may be the same as for the previous heart rate. A particular timing interval may correspond to a range of heart rates, for example, and the interval corresponding to the new heart rate may be the same as the interval corresponding to the previous heart rate. When no change to the interval is needed, the previous interval may be applied (270). Otherwise, a new pacing interval is implemented (278).

The invention offers several advantages. In patients receiving bi-ventricular pacing, bi-atrial pacing or both bi-ventricular and bi-atrial pacing, the invention promotes the hemodynamic performance of the heart by adjusting pacing intervals to achieve good hemodynamic performance. The intervals may be adjusted automatically.

Further, the invention can be adapted to a variety of devices. Bi-ventricular, bi-atrial, three-chamber and four-chamber devices may apply the techniques described above to resynchronize the heart. Moreover, the invention can be adapted to any configuration of electrode placements and is not limited to the electrode placements depicted in FIGS. 2 and 4.

The preceding specific embodiments are illustrative of the practice of the invention. It is to be understood, therefore, that other expedients known to those skilled in the art or disclosed herein may be employed without departing from the invention or the scope of the claims. For example, the techniques of the invention may be employed to synchronize features of the cardiac cycle other than the times ejection commences. The invention may be applied, for example, synchronization the times when maximum flow occurs. Further, as described above, the invention may be applied to set intervals to achieve standards of cardiac performance rather than synchronization of cardiac events.

The invention also encompasses applications in which pacing intervals may be zero or negative. In other words, the order of pacing of complementary chambers may change as heart rate changes. For example, at a low heart rate, the right ventricular pace may be delivered shortly before the left ventricular pace. At a higher heart rate, both ventricles may be paced at the same time. At a still higher heart rate, the order of pacing may be reversed, with the left ventricular pace delivered shortly before the right ventricular pace.

Furthermore, the invention is not limited to A1-A2 and V1-V2 pacing intervals. As noted above, the invention is not limited to a single pacing electrode per chamber, but may be applied to multi-chamber pacing in which there maybe two or more electrodes per chamber. In one application, for example, two electrodes may deliver pacing pulses to the same ventricle, and these pulses need not be delivered simultaneously. Accordingly, there may be a V1-V2 interval, and/or a V1-V3 interval, and/or a V2-V3 interval. The invention may be applied to select any or all of these pacing intervals as a function of heart rate.

The invention further includes within its scope the methods of making and using the systems described above. These methods are not limited to the specific examples described above, but may be adapted to meet the needs of a particular patient. The invention also includes within its scope any of a variety of computer-readable media comprising instructions for causing a programmable processor, such as microprocessor, to carry out the techniques described above. Such computer-readable media include, but are not limited to, magnetic and optical storage media, and read-only memory such as erasable programmable read-only memory or flash memory accessible by the processor. The media may be located in a programmer, for example, or within the implanted device. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable medical device system comprising:
   a pulse generator that delivers a first pacing pulse to a first cardiac chamber of a heart and a second pacing pulse to a second cardiac chamber of the heart following a pacing interval; and
   a processor that selects the pacing interval as a function of a heart rate,
   wherein the first cardiac chamber and the second cardiac chamber are complementary cardiac chambers,
   wherein the pacing interval is a first pacing interval,
   wherein the pulse generator delivers a third pacing pulse to a third cardiac chamber of a heart and a fourth pacing pulse to a fourth cardiac chamber of the heart following a second pacing interval; and
   wherein the processor that selects the second pacing interval as a function of the heart rate.

2. A system according to claim 1, further comprising at less a one of: an accelerometer sensor, an activity sensor and a pressure sensor coupled to the processor, wherein said sensor is adapted to communicate a signal related to patient characteristics.

3. A system according to claim 2, wherein the heart rate is adjusted as a function of a signal generated by at least a one the activity sensor or the accelerometer.

4. A system according to claim 2, wherein at least one of the first pacing interval and the second pacing interval are adjusted based at least in part upon the signal generated by the pressure sensor.

5. A system according to claim 1, further comprising a memory structure that stores a relational data set coupled to the processor, wherein the processor selects at least one of the first pacing interval and the second pacing interval from a plurality of pacing intervals stored in the relational data set based at least in part upon a then-detected heart rate.

6. A system according to claim 1, further comprising memory that stores a formula that defines the pacing interval as a function of the paced heart rate, and wherein the processor selects the pacing interval by applying the formula using the paced heart rate to compute the pacing interval.

7. A system according to claim 6, wherein the memory is configured as a look up table.

8. An implantable medical device system comprising:
   a pulse generator that delivers a first pacing pulse to a first cardiac chamber of a heart and a second pacing pulse to a second cardiac chamber of the heart following a pacing interval; and
   a processor that selects the pacing interval as a function of a heart rate,
   wherein the first cardiac chamber and the second cardiac chamber are complementary cardiac chambers and further comprising a first electrode, a second electrode and a third electrode coupled to the pulse generator, the first electrode disposed in the first cardiac chamber and the second and third electrodes disposed in the second cardiac chamber and wherein
   the pacing interval is a first pacing interval,
   the processor selects a second pacing interval as a function of the heart rate,
   the pulse generator delivers a first pacing pulse to the first cardiac chamber via the first electrode,
   the pulse generator delivers a second pacing pulse to the second cardiac chamber via the second electrode following the first pacing interval, an
   the pulse generator delivers a third pacing pulse to the second cardiac chamber via the third electrode following the second pacing interval.

9. A system according to claim 8, further comprising at least a one of: an accelerometer sensor, an activity sensor and a pressure sensor coupled to the processor, wherein said sensor is adapted to communicate a signal related to patient characteristics.

10. A system according to claim 9, wherein the heart rate is adjusted as a function of a signal generated by at least a one of the activity sensor or the accelerometer.

11. A system according to claim 9, wherein at least one of the first pacing interval and the second pacing interval are adjusted based at least in part upon the signal generated by the pressure sensor.

12. A system according to claim 8, further comprising a memory structure that stores a relational data set coupled to the processor, wherein the processor selects at least one of the first pacing interval and the second pacing interval from a plurality of pacing intervals stored in the relational data set based at least in part upon a then-detected heart rate.

13. A system according to claim 8, further comprising memory at stores a formula that defines the pacing interval as a function of the paced heart rate, and wherein the processor selects the pacing interval by applying the formula using the paced heart rate to compute the pacing interval.

14. A system according to claim 13, wherein the memory is configured as a look up table.

15. A method comprising:

selecting a pacing interval as a function of a heart rate;

delivering a first pacing pulse to a first cardiac chamber of a heart; and delivering a second pacing pulse to a second cardiac chamber of the heart following the pacing interval;

wherein the first cardiac chamber and the second cardiac are complementary cardiac chambers and further comprising:

setting a second heart rate;

selecting a second pacing interval as a function of the second heart rate.

16. A method comprising:

selecting a pacing interval as a function of a heart rate;

delivering a first pacing pulse to a first cardiac chamber of a heart; and delivering a second pacing pulse to a second cardiac chamber of the heart following the pacing interval;

wherein the first cardiac chamber and the second cardiac are complementary cardiac chambers and wherein the pacing interval is first pacing interval, the method further comprising:

delivering a third paving pulse to a third cardiac chamber of a heart; and delivering a fourth pacing pulse to a fourth cardiac chamber of the heart following a second pacing interval.

17. A method comprising:

selecting a pacing interval as a function of a heart rate;

delivering a first pacing pulse to a first cardiac chamber of a heart; and delivering a second pacing pulse to a second cardiac chamber of the heart following the pacing interval;

wherein the first cardiac chamber and the second cardiac are complementary cardiac chambers and wherein the pacing interval is a first pacing interval, the method further comprising delivering a third pacing pulse to one of the first and second cardiac chambers following a second pacing interval.

18. A computer-readable medium comprising instructions that cause a processor to perform a method of cardiac pacing, said medium comprising:

instructions for selecting a pacing interval solely as a function of a paced heart rate;

instructions for delivering a first pacing pulse to a first cardiac chamber of a heart; and instructions for delivering a second pacing pulse to second cardiac chamber of the heart following the pacing interval;

wherein the first cardiac chamber and the second cardiac are complementary cardiac chambers, and further comprising;

instructions for setting a second paced heart rate; and instructions for selecting a second pacing interval as a function of the second heart rate.

19. The medium of claim 18, wherein the pacing interval is a first pacing interval, and further comprising:

instructions for delivering a third pacing pulse to a third cardiac chamber of the heart; and instructions for delivering a fourth pacing pulse to a fourth cardiac chamber of the heart following a second pacing interval.

20. The medium of claim 18 wherein the pacing interval is a first pacing interval, and further comprising instructions ford delivering a third pacing pulse to one of the first and second cardiac chambers following a second pacing interval.

* * * * *

UNITED STATES PATENT AND TRADEMARK OFFICE
CERTIFICATE OF CORRECTION

PATENT NO. : 6,839,592 B2
DATED : January 4, 2005
INVENTOR(S) : Chester L. Struble and Pierre A. Grandjean It is certified that error appears in the above-identified patent and that said Letters Patent is hereby corrected as shown below:

Column 18,
Lines 1 and 2, delete "at less a one of", replace with -- at least a one of --.
Line 8, delete "a one the", replace with -- a one of the --.
Line 51, delete "interval, an", replace with -- interval, and --.

Column 19,
Line 39, delete "paving pulse", replace with -- pacing pulse --.

Column 20,
Line 21, delete "pulse to second", replace with -- pulse to a second --.
Line 40, delete "ford delivering", replace with -- for delivering --.

Signed and Sealed this

Seventh Day of June, 2005

JON W. DUDAS
*Director of the United States Patent and Trademark Office*